United States Patent [19]

Crisman, Jr.

[11] Patent Number: 5,292,195
[45] Date of Patent: Mar. 8, 1994

[54] THERMOGRAPHIC EVALUATION TECHNIQUE

[75] Inventor: Elton M. Crisman, Jr., Saint Cloud, Fla.

[73] Assignee: Martin Marietta Corporation, Bethesda, Md.

[21] Appl. No.: 942,216

[22] Filed: Sep. 9, 1992

[51] Int. Cl.⁵ .......................................... G01N 25/72
[52] U.S. Cl. ..................................... 374/4; 374/124; 374/129; 250/330; 348/164
[58] Field of Search ............... 374/4, 5, 120, 121, 374/124, 129; 250/342, 330; 283/87, 88; 358/106, 113

[56]       References Cited
       U.S. PATENT DOCUMENTS

| | | | |
|---|---|---|---|
| 4,083,223 | 4/1978 | Hashimoto et al. | 374/124 |
| 4,647,220 | 3/1987 | Adams et al. | 374/5 |
| 4,733,079 | 3/1988 | Adams et al. | 250/341 |
| 4,751,571 | 6/1988 | Lillquist | 250/330 |
| 4,768,158 | 8/1988 | Osanai | 374/5 X |
| 4,795,906 | 1/1989 | Adams et al. | 250/341 |
| 4,854,724 | 8/1989 | Adams et al. | 374/5 |
| 4,866,276 | 9/1989 | Leavens et al. | 250/341 |
| 4,872,762 | 10/1989 | Koshihara et al. | 374/124 |
| 4,983,836 | 1/1991 | Matoba et al. | 250/330 |
| 5,032,727 | 7/1991 | Cox, Jr. et al. | 374/5 |
| 5,041,726 | 8/1991 | Chang et al. | 250/341 |
| 5,069,005 | 12/1991 | Hovland et al. | 374/5 X |
| 5,111,048 | 5/1992 | Devitt et al. | 374/5 X |

FOREIGN PATENT DOCUMENTS 2432600 1/1976 Fed. Rep. of Germany .
2168494 6/1986 United Kingdom ............... 374/5

Primary Examiner—William A. Cuchlinski, Jr.
Assistant Examiner—G. Bradley Bennett
Attorney, Agent, or Firm—Burns, Doane, Swecker & Mathis

[57]       ABSTRACT

In a nondestructive thermographic evaluation technique, a selected amount of energy is applied to a first object having a known surface structure. An image of the first object is formed within the dynamic limits of an imaging device which preferably includes a white bar. The image is stored on a recording device and enhanced using an image processor. The selected amount of energy is then applied to a second object which is imaged by the imaging device, and the image of the second object is also enhanced. The images of the first and second objects are then compared to determine whether there are any differences in the surface structure of the two objects.

14 Claims, 4 Drawing Sheets

THERMOGRAPHIC EVALUATION TECHNIQUE

FIELD OF THE INVENTION

The present invention relates to the field of nondestructive evaluation of objects, and more specifically to a technique for thermographically evaluating the surface structure of an object.

BACKGROUND OF THE INVENTION

Thermographic evaluation typically involves irradiating an object with infrared radiation, and then analyzing the heat reflected from the object to determine a particular characteristic of the object. Prior art thermographic evaluation techniques disclosed in U.S. Pat. Nos. 4,733,079 and 4,795,906 provide a method and apparatus for thermographically identifying parts. Identification codes are etched into the parts. Infrared radiation is directed at the parts, and the reflected radiation is analyzed using image processing hardware to identify the code numbers etched into the parts. U.S. Pat. Nos. 4,854,724 and 4,647,220 respectively disclose thermographic techniques for evaluating defects in spot welds and corrosion in metallic surface structures. The evaluation techniques of the aforementioned patents include the application of heat from a pulsating infrared source, scanning the heated surface of the object with a sensing device to determine temperature differentials, and generating an image of the object from the temperature differentials. The resulting images provide an indication whether there are any defects in the spot weld or whether the object is corroded.

These prior art thermographic nondestructive evaluation techniques depend on incremental temperature variations which are detected on the surface of the material under evaluation. The prior art is limited by a minimum resolvable temperature difference (MRTD) of approximately 0.1° C. In other words, a defect must cause a temperature difference of 0.1° C. to be detectable, and many small defects, therefore, go undetected. If the test sample material conducts heat at a high rate, then a large amount of heat input is also required. The local heat rise caused by the defect, however, can often cause the defect to be masked by the heat input to the surface. Once the surface is heated over a few degrees, all but the largest defects will go undetected. Materials which have a low rate of heat transfer, such as most composites materials, compound this problem and reach surface saturation faster, and consequently such materials are more difficult to evaluate especially when evaluating small defects or flaws.

Accordingly, there is a need for a thermographic evaluation technique that can overcome the problems associated with the prior art techniques, that requires less heat and that detects smaller defects or flaws.

SUMMARY OF THE INVENTION

The present invention relates to a nondestructive thermographic evaluation technique which requires substantially less heat and can detect substantially smaller defects or flaws in an object to be evaluated. The technique involves the application of a selected amount of energy to a first object having a known surface structure. The known surface structure may include a known defect or may include a distinctive thermographic signature. The object having the known surface structure is irradiated with infrared energy or a selected amount of heat and imaged with an infrared camera which preferably includes a white bar. The white bar provides an indication that the image is within the dynamic range of the infrared camera. The image of the object having the known surface structure is recorded on a storage device such as a video cassette recorder, and the image may be enhanced using conventional image processing techniques to reveal the known surface structure of the object. Once the selected amount of energy and the image processing techniques have been selected, a second object may be evaluated. The selected amount of energy is applied to the second object. The second object is then imaged using the infrared camera, and the image is enhanced using the same image processing techniques. The image of the second object being evaluated is then compared with the image of the object having the known surface structure, in order to determine whether there are any differences in the surface structure which would indicate the existence of defects or flaws in the second object.

DETAILED DESCRIPTION OF THE INVENTION

Figure 1:
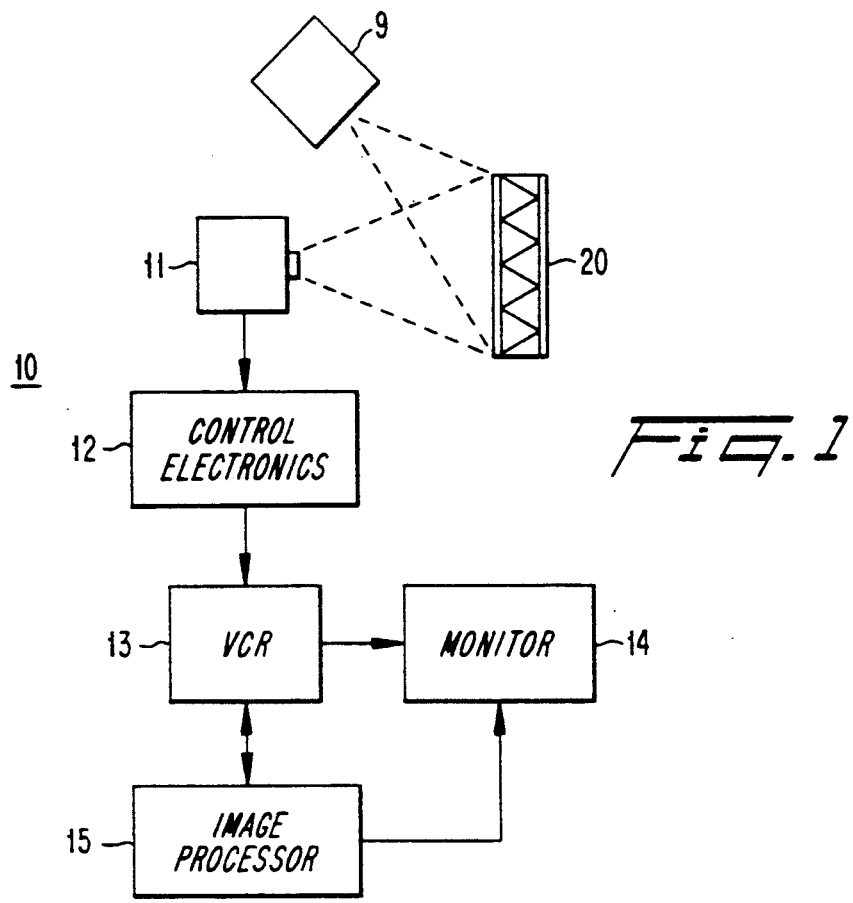
FIG. 1 is a block diagram of the thermographic imaging hardware and an object having a known surface structure.

Referring now to FIG. 1, a block diagram of thermographic imaging hardware 10 and an object 20 having a known surface structure are illustrated. The thermographic imaging hardware 10 preferably includes an energy source 9 and an imaging device 11 which is used for forming an image of the object 20. It is important that the image be as clean, noise-free and focussed as possible in order to extract the most information. The purpose of the energy source 9 is to uniformly heat the surface of the object 20 and to cause the surface to radiate infrared energy having wavelengths in the range of 8 to 12 microns. The energy source 9 may include a quartz lamp, a xenon flash light, a heating element, a moveable light mounted on a track, a container of warm fluid or the like. Preferably, infrared energy having wavelengths in the range of 0.4 to 2 microns is emitted from the energy source 9. It is desirable that the energy source 9 emits infrared energy having wavelengths in a first range and that the object radiates infrared energy having different wavelengths in a second range. The particular energy source 9 selected for use with the present invention will ordinarily be determined through trial and error.

The imaging device 11 is preferably a high quality infrared camera of a type well known in the art and manufactured by Inframetrics Company, except that the infrared camera includes a white bar whose significance will be hereinafter described in greater detail. The white bar is a bar which appears on the image and goes from white saturated to black saturated. In some instances, it may be desirable to assign pseudo-colors to the range of values associated with the white bar. Preferably, energy radiated from the object 20 has wavelengths in 8 to 12 microns range which is picked up by the mercury cadmium telluride detectors of the imaging device 11. The imaging device 11 may also include a timing device which will act as a shutter to allow the detector to be exposed for a short period of time such as 1/1000 of a second. The imaging device 11 may be any scanner or focal plane array which is suitable for the task.

The output of the imaging device 11 is supplied to control electronics 12 which in turn is coupled to a video cassette recorder 13 that records the output of the imaging device 11. Instead of storing analog images on the video cassette recorder 13, it is possible to store digital images on a digital recording device. In the practice of the present invention, sixty fields or thirty frames per second are typically created, resulting in the storage of an enormous amount of information. Accordingly, cost considerations will ordinarily dictate the use of an analog storage device such as a Super VHS VCR 13 operated at a neutral setting.

The images recorded on the VCR 13 can be supplied directly to a monitor 14 for viewing, or the images can be supplied to an image processor 15. The image processor 15 is a suitably programmed special purpose digital computer that is capable of enhancing and manipulating the images from the VCR 13. The monitor 14 may be a monochrome (black and white) monitor, or alternatively the monitor may be a color monitor equipped with a suitable colorizer. Preferably, the monitor is a high resolution 2,000 line black and white monitor. The use of color monitors in thermographic imaging systems is well known to those skilled in the art. The principles of the present invention may be practiced using either a monochrome or color monitor.

Figure 2:
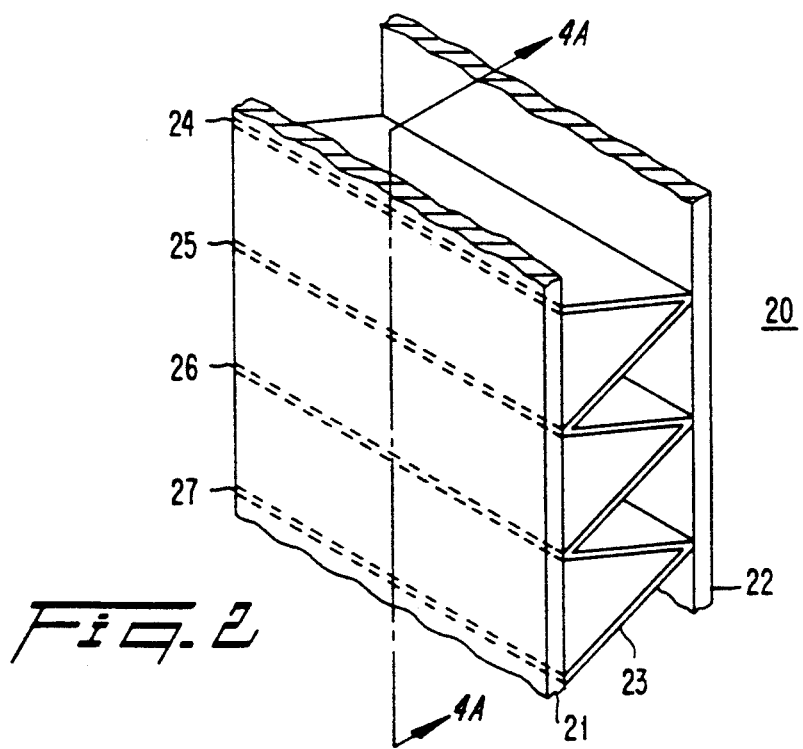
FIG. 2 is a perspective view of an object having the known surface structure.

Referring now to FIG. 2, there is a perspective view of a representative object 20 which is suitable for thermographic evaluation using the techniques of the present invention. The object 20 is formed from a pair of parallel metal plates 21 and 22. Disposed between the pair of metal plates 21, 22 is a reinforcing web 23 which is spot welded to the parallel plates. When the reinforcing web 23 is correctly spot welded to the plate 21 a series of spot welds 24, 25, 26, 27 will be formed on the interior surface of plate 21 as indicated by the dotted lines.

Figure 3A:
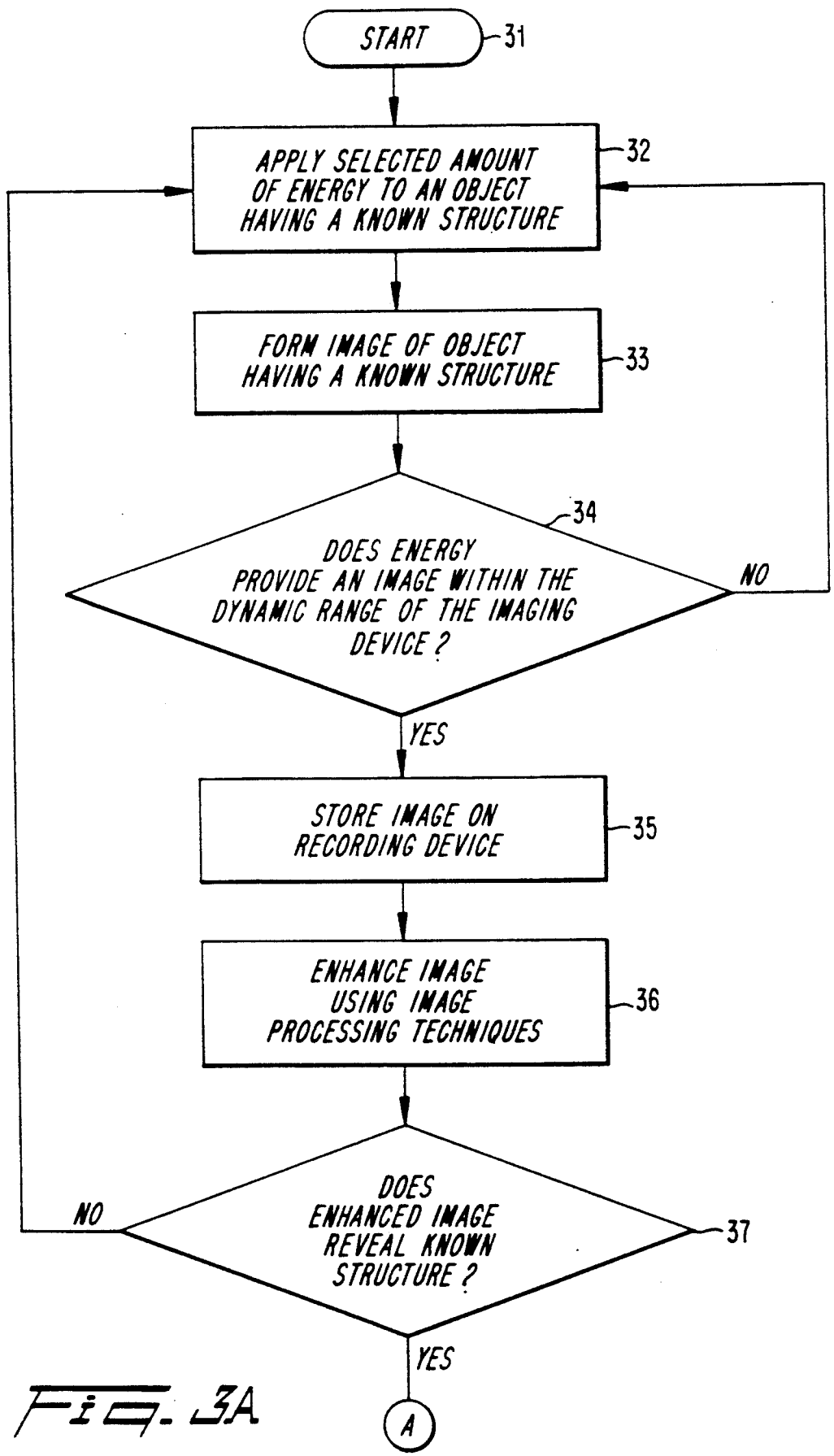
FIGS. 3A and 3B are flow diagrams illustrating the thermographic evaluation technique of the present invention.
Figure 3B:
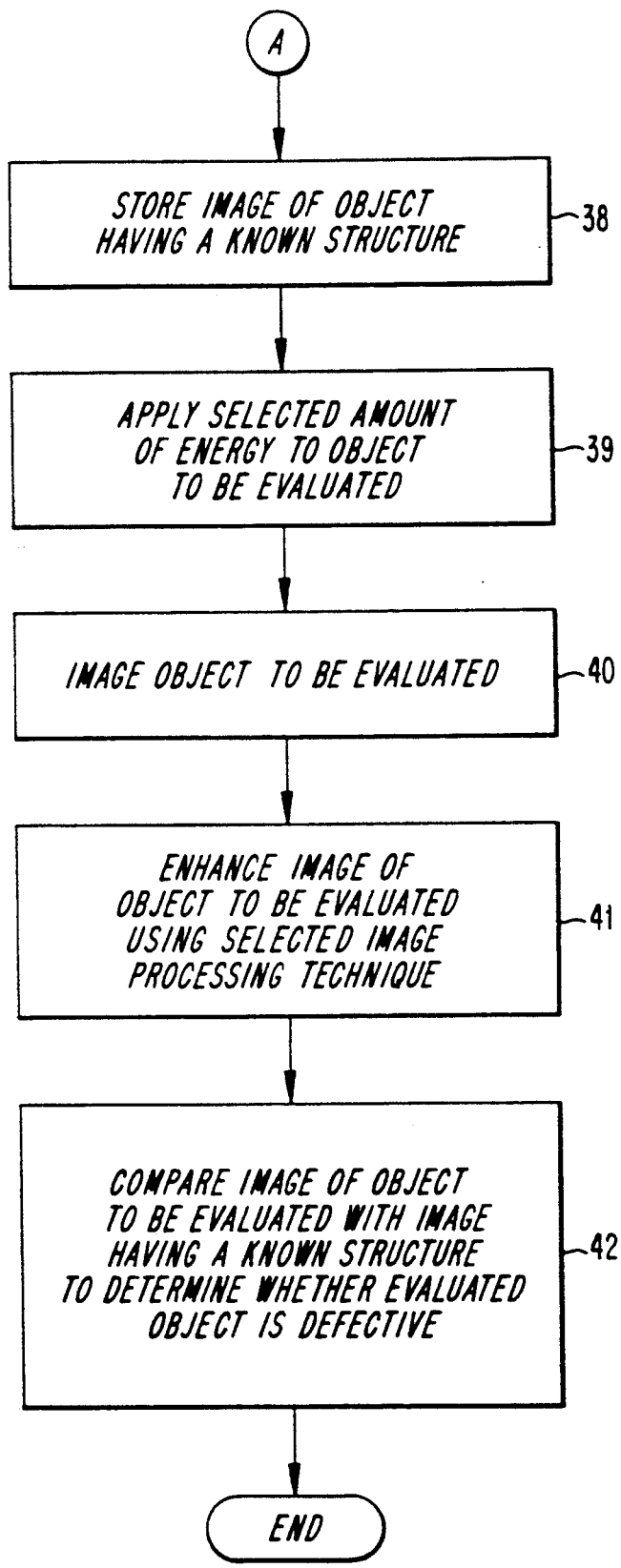

Referring now to FIGS. 3A and 3B, a flow diagram illustrates the steps of the thermographic evaluation technique of the present invention. The thermographic evaluation technique of the present invention includes a starting step 31 in which an object having a known surface structure is selected. The known surface structure of the object may either be a surface structure which includes a defect or a surface structure which includes a distinctive thermographic signature. For example, if the surface structure is a pipe having a uniform thickness which does not provide a distinctive thermographic signature, it is desirable to start with a pipe having a known defect, such as a graduated indentation on the inner surface of the pipe. On the other hand, if the surface structure includes a distinctive thermographic signature, such as the reinforced metallic structure of FIG. 2, then it may be preferable to start with a known surface structure which is free of any defects.

The next step 32 of the thermographic evaluation technique involves applying a selected amount of energy to the object having a known surface structure. When heat is applied to the object, it is applied for a predetermined amount of time. Accordingly, the selected amount of energy is a function of a predetermined heat flow for a predetermined amount of time. The purpose of applying a selected amount of energy is to uniformly raise the temperature of the surface of the object. In most instances, the surface of the object will be raised approximately 5 to 10 degrees over the ambient temperature. In order to apply a uniform amount of heat to the surface numerous techniques may be used. The best technique will be the result of trial and error experimentation. In some instances a hand held quartz lamp may be used to illuminate the object. In other instances a heat source may be placed on a moving track which moves the heat source across the front of the object and causes the front surface to be uniformly heated. In at least one instance which involved an irregularly contoured surface, the most effective method for uniformly heating the irregularly contoured surface involved a rubber bladder filled with warm water. Another illumination technique includes the use of a 9800 watt-second xenon flash lamp. The particular technique for heating the object having a known surface structure must be arrived at empirically.

In step 33, an image of the object 20 having the known surface structure is formed using the hardware illustrated in FIG. 1. In other words, heat is applied to the object 20, and the imaging device 11 forms an image of the object 20. The image from the imaging device 11 may be viewed directly on the monitor 14 or stored on the VCR 13 and evaluated later.

Figure 4A:
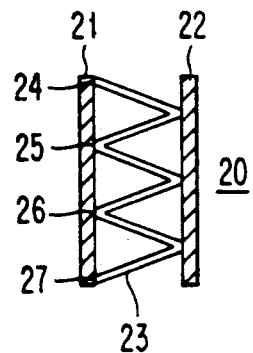
FIG. 4A is a cross-sectional view of the object having the known surface structure illustrated in FIG. 2.
Figure 4B:
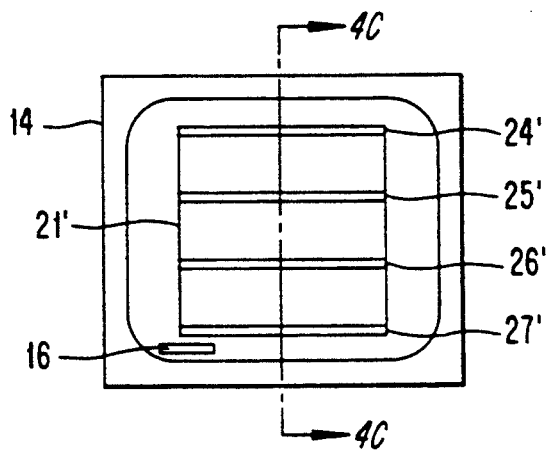
FIG. 4B is an illustration of a thermographic image of the surface structure of FIG. 4A displayed on a monitor.

In step 34, a determination is made whether the energy applied to the object 20 provides an image within the dynamic range of the imaging device 11. The operator of the hardware 10 can make this determination by using the white bar of the camera 11. The camera 11 includes a white bar 16 which is displayed on the monitor 14, as illustrated in FIGS. 4B and 4E. If the camera 11 is an 8 bit camera, the camera is capable of generating 256 steps on a gray scale which goes from white to black. Due to recent advances in camera technology, 12, 14 and even 16 bit cameras are becoming available for use with the present invention, and the higher resolution cameras would include white bars having substantially more steps. The white bar 16, therefore, provides a visual indication of how many of these steps are being used to form the image, and the white bar further provides an indication of the dynamic range of the camera. If too much heat has been applied to the object, the white bar 16 provides a good indication that the image is saturated. For example, if the operator applies too much heat to the object in step 32, the operator will see a very dark image on the monitor 14, and the scale of the white bar 16 will exceed its maximum limit, thereby indicating that the image is saturated and that data is being lost. If too little heat is applied, the scale of the white bar 16 will indicate that the maximum limit has not yet been reached. Accordingly, in step 34 the operator determines when the image of the object is within the dynamic range of the camera 11 by viewing the actual image and ensuring that the scale of the white bar reaches its maximum limit. If the operator determines that the amount of selected heat does not provide an image within the dynamic range of the camera 11, then step 32 is performed again by applying a different amount of selected heat. If the operator, however, determines that the amount of selected energy is within the dynamic range of the camera 11, then step 35 is performed.

In step 35, the image of the object having a known surface structure is stored on a recording device such as the VCR 13. No image processing is done on the image prior to storage of the image on the VCR 13. Once the image is stored on the recording device, it is desirable to run the stored signal through a time based corrector that puts a perfect synch signal back on each field of the stored image. The synch signal is particularly helpful when a shuttering device has been used to form the image, the shuttering can be keyed to the synch signal. A shuttering device may be desirable when a xenon flash lamp is used as the energy source 9.

In step 36, the stored image is enhanced using known image processing techniques. The image processing techniques are performed by the image processor 15. The image processing techniques include convolution filtering, Laplacian transformations, second order derivatives, edge enhancements or any other well known image processing technique which enhances the image. The primary image enhancement technique includes convolution filtering which involves the use of $3 \times 3$ up to $25 \times 25$ matrices. The particular image enhancement technique is a matter of trial and error, and it will depend upon the surface structure of the object being imaged.

In step 37, the operator evaluates the enhanced image to determine whether the enhanced image reveals the known surface structure. The purpose of step 37 is to establish a standard for the known surface structure. For example, if the known surface structure is a uniform pipe having a predetermined indentation on the inner surface of the pipe, and if the operator can clearly see the indentation, then the operator makes the determination that the defect in the known surface structure is clearly revealed. If for example, the known surface structure has a distinctive thermographic signature, such as the object 20 of FIG. 2, then the operator can make the determination that the enhanced image reveals the known surface structure. The distinctive thermographic signature of the object 20 will hereinafter be described in connection with FIGS. 4A through 4B.

Referring now to FIG. 3B, the remaining steps of the thermographic evaluation technique of the present invention will now be explained. In step 38 the enhanced image of the object having the known surface structure is stored. The image may be stored in a recording device such as the VCR 13, or the image may be digitized and stored in an electronic memory. The stored enhanced images provide a data base of images which are useful for comparing to images of other objects to determine whether these other objects have a surface structure similar to the object having the known surface structure. In other words, the stored enhanced image is a standard which can be compared to a similar object having an unknown surface structure.

In Step 39 an object to be evaluated is placed in front of the imaging device 11, and the selected amount of energy determined in Step 32 is applied to this second object. In Step 40 the object to be evaluated is imaged using the imaging device 11. The primary reason for imaging the second object is to determine whether the surface structure of the second object includes any flaws or defects. The image acquired in Step 40 is then enhanced using the image processor 15 and the same image enhancement processing techniques determined in Step 36.

In Step 42, the enhanced image of the second object being evaluated is then compared with the enhanced image stored in Step 38 to determine whether the evaluated object is defective or whether there is a difference in surface structure between the two images. The determination of Step 42, may be made visually by the operator when viewing the monitor 14 and comparing the images of the first object having the known surface structure and the second object being evaluated. The visual comparison may be made by viewing two different monitors, a split screen side-by-side comparison, or sequentially viewing the images of the first and second objects. Alternatively, the comparison may be performed by a suitably programmed computer which analyzes digitized images of Steps 38 and 41.

The present invention will now be explained in conjunction with an example of an object having a known surface structure which exhibits a distinctive thermographic signature. In FIG. 4A, there is a cross-sectional view of the object 20 taken along the line 4A—4A of FIG. 2. FIG. 4A depicts the parallel plates 21, 22 having the reinforcing web 23 spot welded between the two plates. When the object 20 of FIG. 4A is thermographically imaged and displayed on the monitor 14 as shown in FIG. 4B, the rectangular plate image 21' appears on the display screen with four horizontal lines 24', 25', 26', 27' which correspond to the series of spot welds 24, 25, 26, 27. Accordingly, the object 20 provides an image having a distinctive thermographic signature which indicates that the reinforcing web 23 is correctly spot welded to the plate 21.

In order to assist the operator of the thermographic imaging hardware 10, it may be desirable to project graphical representations of the images acquired in Steps 36 and 41. FIG. 4C represents a curve 51 or graphical representation of the cross section of the image 21' of the object 20 acquired during Step 36. Since the object 20 includes a series of correctly welded spot welds 24, 25, 26, 27, the image 21' of plate 21 on monitor 14 as illustrated in FIG. 4B includes four horizontal lines 24', 25', 26', 27'. Digitized data taken along the cross-section represented by the line 4C—4C of FIG. 4B can be used to generate the curve 51 of the type depicted in FIG. 4C. Accordingly, the curve 51 having four spikes which correspond to the horizontal lines 24', 25', 26', 27' may be generated. If desired the curve 51 may be displayed on the monitor 14 along with the image 21' of plate 21.

Figure 4D:
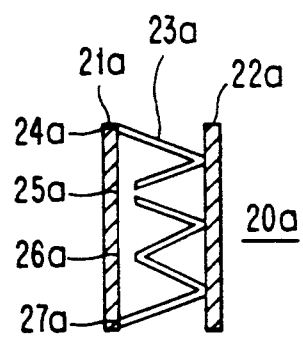
FIG. 4D is a cross-sectional view of an object having a defect.
Figure 4E:
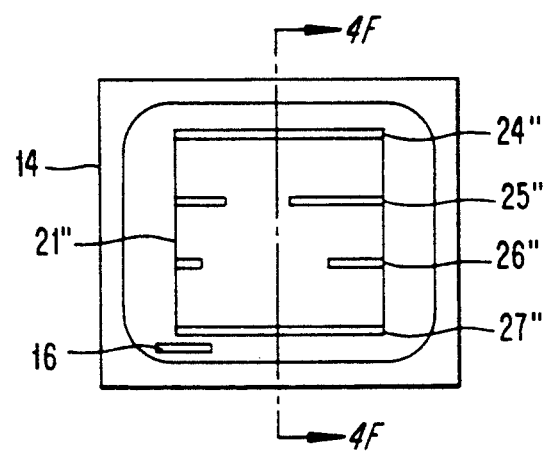
FIG. 4E is an illustration of a thermographic image of the surface structure of FIG. 4D displayed on a monitor.
Figure 4C:
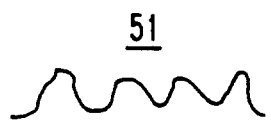
FIG. 4C is a graphical representation of the image data taken along line 4C—4C of FIG. 4B.
Figure 4F:
FIG. 4F is a graphical representation of the image data taken along line 4F—4F of FIG. 4E.

Referring now to FIG. 4D, it can be appreciated that the object 20a includes a series of spot welds 25a, 26a that do not correctly join the reinforcing web 23a to the front plate 21a. In Step 39 of the present invention, the selected amount of energy determined in step 32 is applied to object 20a. Then in step 40 the image of object 20a is formed, and the image is enhanced in step 41 and displayed on monitor 14 as depicted in FIG. 4E. The image 21" displayed on the monitor 14 includes four horizontal lines 24", 25", 26", 27". The image 21" may now be compared to the image 21'. Since the horizontal lines 24", 27" are substantially continuous, like horizontal lines 24', 27', the image 21" indicates that the series of spot welds 24a and 27a are correctly formed. Since the horizontal lines 25", 26" are discontinuous, unlike horizontal lines 25', 26', the image 21" of FIG. 4E indicates that the series of welds 25a, 26a are incorrectly formed between the reinforcing web 23a and the front plate 21a. Digitized data corresponding to the cross-section taken along line 4F—4F of FIG. 4E can be used to generate the curve 52 or graphical representation depicted in FIG. 4F. The curve 52 includes only two spikes which correspond to the series of spot welds 24a and 27a. The absence of spikes corresponding to spot welds 25a and 26a provides an additional indication that the object 20a includes defective spot welds. Accordingly, the operator of the thermographic imaging hardware 10 can make an evaluation of the image 21" of object 20a by visually comparing the images 21', 21" appearing on the monitor 14 or by comparing the graphical representations 51, 52 of the cross-sections of the images 21', 21".

While the present invention has been explained using the metallic surface structure illustrated in FIG. 2, the present invention is not limited to evaluating defects such as spot welds and corrosion in metallic surface structures. It has also been discovered that the present invention is especially well suited for evaluating composite materials made from a plurality of plies. The present invention is capable of imaging disbonds between the plies or inclusions. Moreover, the present invention can be used to determine between which ply the disbond or the inclusion occurs. It has also been discovered that the present invention can be used to evaluate defects in radar absorbing materials. Radar absorbing materials can be evaluated by using a microwave energy source as the energy source 9 of FIG. 1 to generate heat within the radar absorbing material. It has been further discovered that the present invention is also particularly well suited for evaluating the thickness of laminar objects such as grease layers or polymer films. The thickness of a known grease layer or polymer film is first determined, and then a grease layer or polymer film of unknown thickness is compared to the object of known thickness. The particular objects described in the present application are only representative examples of the many objects which can be thermographically evaluated using the principles of the present invention.

While the invention has been described in its preferred embodiments, it should be understood that the words that have been used are words of description rather than of limitation, and that changes within the purview of the present claims may be made without departing from the true scope of the invention in its broader aspects.

I claim:

1. A method for thermographically evaluating objects, comprising the steps of:

(a) applying a selected amount of energy to a first object having a known surface structure in order to raise the surface temperature of the first object;
   (b) imaging the first object having a known surface structure and ensuring that the thermographic imaging device substantially reaches the maximum limit of its dynamic range when imaging the known surface structure;
   (c) recording on a storage device the image of the first object having the known surface structure;
   (d) enhancing the recorded image of the first object to reveal the known surface structure;
   (e) applying the selected amount of energy to a second object to be evaluated in order to raise the surface temperature of the second object;
   (f) imaging the second object with the thermographic imaging device;
   (g) enhancing the image of the second object; and
   (h) comparing the recorded image of the first object having the known surface structure to the image of the second object to be evaluated, in order to determine whether there are any differences in the surface structure of the second object.

2. A method according to claim 1 wherein the dynamic range of the imaging device is determined with a white bar.

3. A method according to claim 2 wherein the imaging device includes an infrared camera.

4. A method according to claim 1 wherein the selected amount of energy raises the surface temperatures of the first and second objects in the range of approximately 5 to 10 degrees.

5. A method according to claim 1 wherein the comparison step includes the generation of graphical representations of the first object and the second object.

6. A method according to claim 1 wherein the known surface structure includes a defect.

7. A method according to claim 6 wherein the defect is a predetermined indentation.

8. A method according to claim 6 wherein the defect is a corroded area.

9. A method according to claim 6 wherein the defect includes at least a first disbond and a first inclusion in a composite material.

10. A method according to claim 1 wherein the known surface structure includes a distinctive thermographic signature.

11. A method according to claim 10 wherein the distinctive thermographic signature is that of a spot weld.

12. A method according to claim 10 wherein the distinctive thermographic signature is that of a grease film.

13. A method according to claim 10 wherein the distinctive thermographic signature is that of a polymer film.

14. A method according to claim 10 wherein the distinctive thermographic signature is that of a radar absorbing material.

* * * * *